(12) United States Patent
Yang

(10) Patent No.: US 11,103,511 B2
(45) Date of Patent: Aug. 31, 2021

(54) SUBSTITUTED INDOLO[2,1-B]QUINAZOLINES AS INHIBITORS OF TRYPTOPHAN DIOXYGENASE AND INDOLEAMINE 2,3-DIOXYGENASE 1

(71) Applicant: FUDAN UNIVERSITY, Shanghai (CN)

(72) Inventor: Qing Yang, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 16/619,880

(22) PCT Filed: Jun. 5, 2018

(86) PCT No.: PCT/CN2018/089989
§ 371 (c)(1),
(2) Date: Dec. 5, 2019

(87) PCT Pub. No.: WO2018/223969
PCT Pub. Date: Dec. 13, 2018

(65) Prior Publication Data
US 2020/0101075 A1 Apr. 2, 2020

(30) Foreign Application Priority Data
Jun. 5, 2017 (CN) .......................... 201710414153.4

(51) Int. Cl.
*C07D 487/22* (2006.01)
*A61K 31/519* (2006.01)
*A61K 31/5377* (2006.01)

(52) U.S. Cl.
CPC ........ *A61K 31/519* (2013.01); *A61K 31/5377* (2013.01)

(58) Field of Classification Search
CPC ........................... A61K 31/519; C07D 487/22
USPC .......................................... 514/257; 544/246
See application file for complete search history.

(56) References Cited

U.S. PATENT DOCUMENTS

2016/0297822 A1\* 10/2016 Yang ....................... A61P 25/00

FOREIGN PATENT DOCUMENTS

| CN | 102532144 A | 7/2012 |
| CN | 103570726 A | 2/2014 |
| CN | 103570727 A | 2/2014 |
| WO | 2017/034420 A1 | 3/2017 |
| WO | 2017/173973 A1 | 10/2017 |

OTHER PUBLICATIONS

Jordan, V. C. Nature Reviews: Drug Discovery, 2, 2003, 205.\*
Hackam, et al. JAMA, 296(14), 2006, 1731-1732.\*

\* cited by examiner

*Primary Examiner* — Douglas M Willis
(74) *Attorney, Agent, or Firm* — Novick, Kim & Lee, PLLC; Zhi Yang Xue; Bin Lu

(57) ABSTRACT

The present invention provides an application of N-benzyl tryptanthrin derivative as tryptophan dioxygenase (TDO) inhibitor, and more specifically an application of N-benzyl tryptanthrin derivative or a pharmaceutically acceptable salt thereof. Said derivative has a structural general formula as represented by formula 1, wherein each group is defined as in the specification. The derivative of the present invention has a good TDO inhibiting activity and can be used to prepare a treatment for diseases associated with TDO activity and expression.

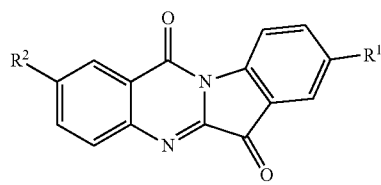

8 Claims, No Drawings

SUBSTITUTED INDOLO[2,1-B]QUINAZOLINES AS INHIBITORS OF TRYPTOPHAN DIOXYGENASE AND INDOLEAMINE 2,3-DIOXYGENASE 1

FIELD OF THE INVENTION

The present invention relates to the field of medicinal chemistry and specifically, relates to a use of N-benzyl tryptanthrin derivative as TDO inhibitor.

BACKGROUND OF THE INVENTION

There are three first rate-limiting enzymes in mammals that catalyze the catabolism of essential amino acid L-tryptophan (L-tryptophan L-Trp) through kynurenine pathway (KP), which are tryptophan 2, 3-dioxygenase (TDO), indoleamine 2, 3-dioxygenase 1, (IDO1), and indoleamine 2, 3-dioxygenase 2 (indoleamine 2 , 3-dioxygenase 2, IDO2).

TDO (or TDO 2, EC.1.13.11.11) is a heme-containing multimeric dioxygenase present in cells, which is consisted of four same heme-containing subunits. It was first founded in rabbit liver in 1936. TDO, mainly distributed in the liver and brain of mammals, and also expressed in other parts such as skin and placenta after stimulation. Exogenous tryptophan, kynurenine (kynurenine, Kyn) and glucocorticoid can induce the expression of endogenous TDO2 gene. The human TDO coding gene (Tdo or Tdo2) is located on chromosome 4 (4q32.1) with a total length of about 16 KB and contains 12 exons and 11 introns. The monomer protein thereof has a molecular weight of about 46.7 kDa and is consisted of 406 amino acids. Both eukaryotic and prokaryotic TDO have high catalytic activity on L-Trp while having very low catalytic activity on D-Trp. Although TDO and IDO1 catalyze the same biochemical reaction pathway, their substrate specificity is different. TDO specifically catalyzes L-tryptophan and its specific derivatives. IDO1 can catalyze a series of substrates, L-tryptophan, D-tryptophan, 5-hydroxytryptamine, etc.

The sequence similarity between TDO and IDO1 is very low, but the heme-containing active site in TDO and IDO1 is highly similar. In recent years, it has been found that TDO is related to tumor immune escape, and the increase of TDO activity results in a significant increase in the content of tryptophan metabolites, such as kynurenine, etc, thereby increasing the level of regulatory T cells in vivo and generating immune tolerance. Kynurenine can bind and activate aromatic hydrocarbon receptors and increase tumor cell survival rate to help tumor cells immune escape.

Although TDO and IDO1 play similar roles in tryptophan metabolism, there are very few studies on the application of TDO inhibitors in oncology. Until 2011, studies showed the relationship between TDO and gliomas. Experimental data showed that TDO expression was significantly up-regulated in glioma cell lines. Knocking down the expression of IDO1 and IDO2 by means of genetic engineering did not affect tryptophan metabolism level in cells, while knocking down TDO expression would reduce the amount of kynurenine produced through the kynurenine pathway, thus confirming the significance of TDO in tryptophan metabolism of glioma. The study clarified the role of TDO in oncology, and took it as a disease target. Other experiments have reported that some serious brain diseases such as Alzheimer's and schizophrenia are also related to TDO enzymes. Studies have found that TDO is expressed in neurons, brain blood vessels and astrocytes in patients with schizophrenia, and the inhibition of the kynurenine pathway can effectively treat various cognitive diseases such as bipolar disorder and Alzheimer's disease. Other experiments have reported that some serious brain diseases such as Alzheimer's and schizophrenia are also related to TDO enzymes.

Studies have shown that TDO is over-expressed in most tumor cell lines, such as bladder cancer, liver cancer, melanoma, lung cancer, colon cancer, myeloma, leukemia, and pancreatic cancer. In tumor cells, TDO-catalyzed tryptophan catabolism is the material basis of immunosuppressive response. This mechanism can promote the survival, growth, differentiation and metastasis of malignant cells, such as bladder cancer, hepatocarcinoma, melanoma, etc. In some tumor cell lines that constitutively express TDO, IDO1 and IDO2 have little effect in mediating tryptophan metabolism. The important role of TDO in tumor regulation has been clearly demonstrated by researchers using P815 tumor model, and inhibition of TDO has been shown to effectively control tumor growth. Such findings provide a scientific basis for the possible application of TDO inhibitors in the treatment of tumor diseases. Therefore, TDO inhibitors are potential drugs for treating diseases related to abnormal expression or activation of TDO.

In summary, there is an urgent need in the art to develop new TDO inhibitors so as to provide new drug targets and ideas for treatment of severe diseases mediated by TDO only (such as liver cancer, glioma, and mental disorders) or IDO1 and TDO (multiple cancers, Alzheimer's).

SUMMARY OF THE INVENTION

The present invention provides a use of N-benzyl tryptanthrin derivative in inhibiting TDO.

In the first aspect of the present invention, a use of N-benzyl tryptanthrin derivative of formula A1, or a pharmaceutically acceptable salt thereof in preparing a pharmaceutical composition or formulation for inhibiting TDO activity is provided, the structural general formula of the derivative is as follows:

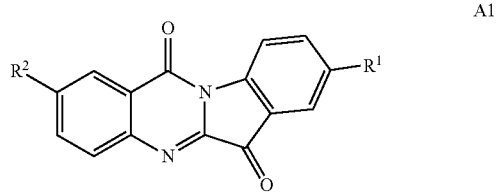

Wherein, $R^1$ is selected from the group consisting of hydrogen, fluorine, -(substituted or unsubstituted C1-C6 alkyl) -substituted or unsubstituted 5-12 membered heterocyclyl; wherein, the heterocyclyl contains 1-3 heteroatoms selected from N, O or S;

$R^2$ is selected from the group consisting of H, Cl, Br, substituted or unsubstituted C1-C4 alkyl, —$NR^3R^4$, or -(substituted or unsubstituted C1-C6 alkyl)—$NR^3R^4$;

$R^3$ and $R^4$ are each independently selected from the group consisting of H, substituted or unsubstituted C1-C4 alkyl, substituted or unsubstituted C2-C4 alkenyl, substituted or unsubstituted C2-C4 alkynyl, substituted or unsubstituted C3-C6 cycloalkyl;

or $R^3$, $R^4$ and adjacent nitrogen atoms together form a substituted or unsubstituted 5-12 membered heterocyclyl, wherein, the 5-12 membered heterocyclyl has 1-2 nitrogen atoms, and 0-2 heteroatoms selected from O, S;

the "substituted" means that one or more hydrogen atoms (preferably hydrogen atoms on the nitrogen atom) on the groups are substituted by substituents selected from the group consisting of C1-C4 alkyl, C1-C4 haloalkyl, amine protecting group (preferably tert-butoxycarbonyl), halogen, phenyl.

In another preferred embodiment, the heterocyclyl is a saturated heterocyclyl, partially unsaturated heterocyclyl, or completely unsaturated heterocyclyl (aromatic group).

In another preferred embodiment, when $R^2$ is H, Cl, Br, substituted or unsubstituted C1-C4 alkyl, $R^1$ is -(substituted or unsubstituted C1-C6 alkyl)-substituted or unsubstituted 5-12 membered heterocyclyl, and when $R^1$ is hydrogen or fluorine, $R^2$ is -(substituted or unsubstituted C1-C6 alkyl)-$NR^3R^4$.

In another preferred embodiment, the 5-12 membered heterocyclyl is selected from the group consisting of substituted or unsubstituted pyridine, substituted or unsubstituted pyrimidine, substituted or unsubstituted pyridazine, substituted or unsubstituted tetrazine, substituted or unsubstituted pyrrole, substituted or unsubstituted thiophene, substituted or unsubstituted furan, substituted or unsubstituted triazole, substituted or unsubstituted imidazole, substituted or unsubstituted thiazole, substituted or unsubstituted oxazole, substituted or unsubstituted pyrazole, substituted or unsubstituted isothiazole, substituted or unsubstituted isoxazole, substituted or unsubstituted oxadiazole, substituted or unsubstituted thiadiazole, substituted or unsubstituted substituted indole, substituted or unsubstituted indazole, substituted or unsubstituted quinoline, substituted or unsubstituted isoquinoline, substituted or unsubstituted benzofuran, substituted or unsubstituted benzothiophene, substituted or unsubstituted benzimidazole, substituted or unsubstituted benzoxazole, substituted or unsubstituted benzothiazole, substituted or unsubstituted benzoisothiazole, substituted or unsubstituted benzoisoxazole, substituted or unsubstituted benzotriazole, substituted or unsubstituted morpholine, substituted or unsubstituted dihydropiperidine, substituted or unsubstituted thiomorpholine, substituted or unsubstituted piperidine, substituted or unsubstituted piperazine, substituted or unsubstituted tetrahydropyran, substituted or unsubstituted dihydropyran, substituted or unsubstituted pyrroline, substituted or unsubstituted tetrahydrothiophene, substituted or unsubstituted tetrahydrofuran, substituted or unsubstituted oxetane, substituted or unsubstituted thietane, substituted or unsubstituted azetidine.

In another preferred embodiment, the 5-12 membered heterocyclyl is a substituent formed by the ring selected from the group consisting of

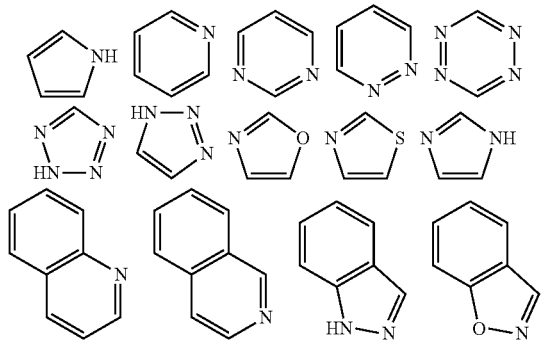

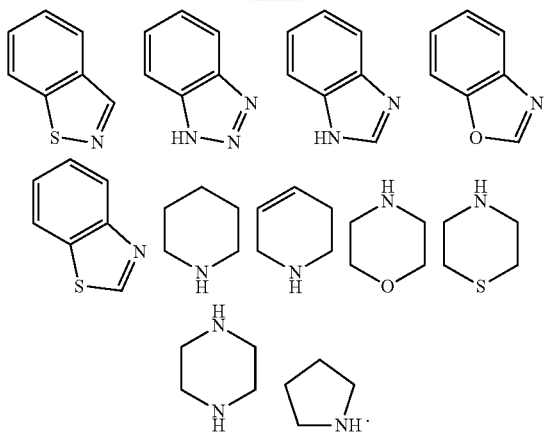

In another preferred embodiment, $R^2$ is selected from the group consisting of

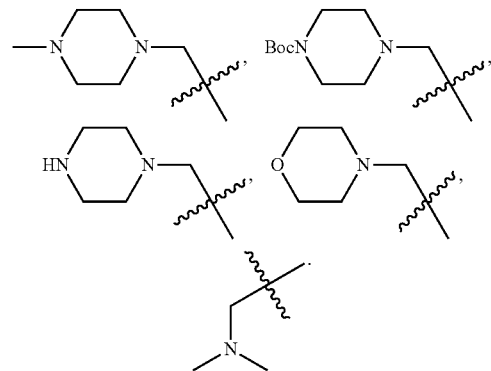

In another preferred embodiment, the derivative is selected from the following compounds:

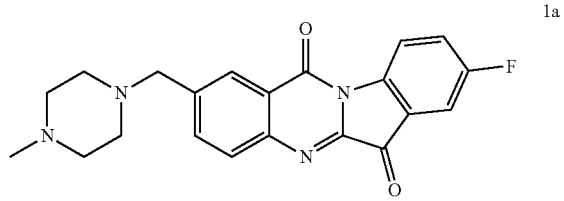

1a

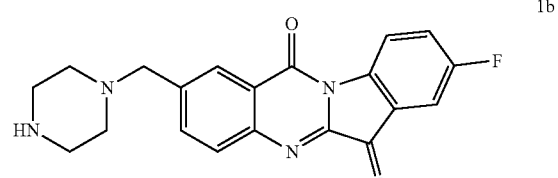

1b

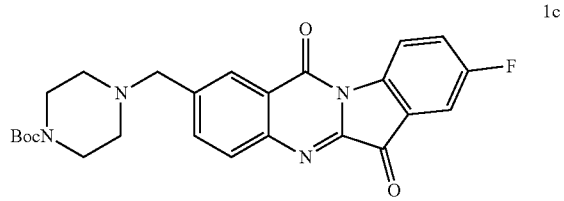

1c

-continued

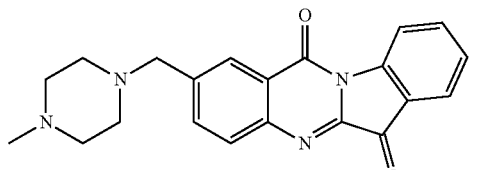
1d

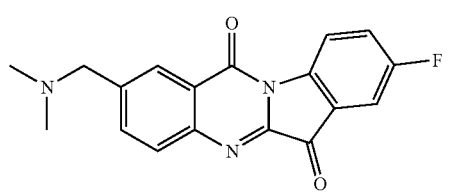
1e

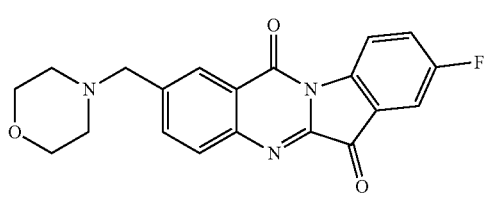
1f

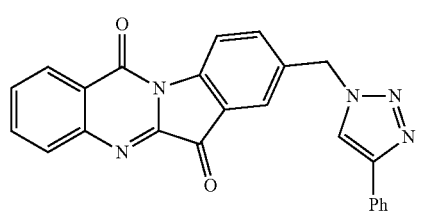
3a

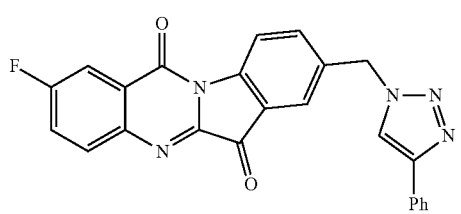
3b

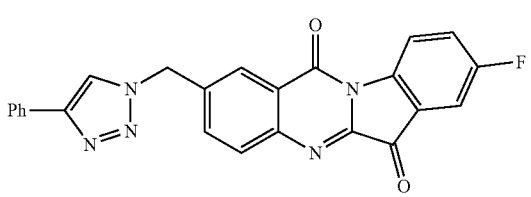
3c

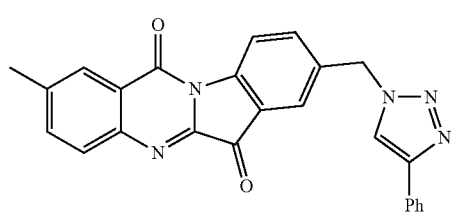
3d

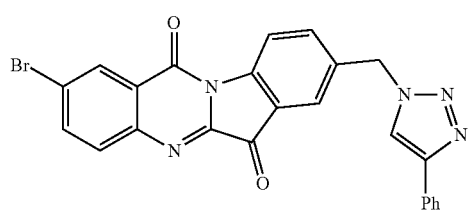
3e

-continued

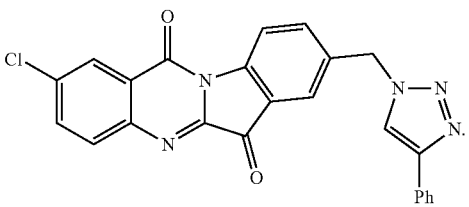
3f

In another preferred embodiment, the pharmaceutical composition or formulation is used to inhibit tryptophan dioxygenase (TDO) activity.

In another preferred example, the pharmaceutical composition or formulation is further used to inhibit indoleamine 2,3-dioxygenase 1 (IDO1) activity.

In another preferred embodiment, the pharmaceutical composition or formulation is further used to inhibit indoleamine 2,3-dioxygenase 1 (IDO1) activity and tryptophan dioxygenase (TDO) activity.

In another preferred embodiment, the TDO is human TDO.

In another preferred example, the pharmaceutical composition is further used to treat TDO-related diseases.

In another preferred embodiment, the "TDO-related diseases" comprise diseases mediated by TDO only, or diseases mediated by both of IDO1 and TDO.

In another preferred embodiment, the disease with pathological characteristics of tryptophan metabolism disorders of TDO-related diseases is selected from the group consisting of tumors with no expression of IDO1, such as liver cancer, glioma, and mental disorders.

In the second aspect of the present invention, a TDO inhibitor is provided, comprising N-benzyl tryptanthrin derivative of formula A1, or a pharmaceutically acceptable salt thereof according to the first aspect of the invention.

In the third aspect of the present invention, a N-benzyl tryptanthrin derivative of formula A1, or a pharmaceutically acceptable salt is provided;

A1 wherein, $R^1$ is selected from the group consisting of hydrogen, fluorine, -(substituted or unsubstituted C1-C6 alkyl)-substituted or unsubstituted 5-12 membered heterocyclyl; wherein, the heterocyclyl contains 1-3 heteroatoms selected from N, O or S;

$R^2$ is selected from the group consisting of H, Cl, Br, substituted or unsubstituted C1-C4 alkyl, —$NR^3R^4$, or -(substituted or unsubstituted C1-C6 alkyl)—$NR^3R^4$;

$R^3$ and $R^4$ are each independently selected from the group: H, substituted or unsubstituted C1-C4 alkyl, substituted or unsubstituted C2-C4 alkenyl, substituted or unsubstituted C2-C4 alkynyl, substituted or unsubstituted C3-C6 cycloalkyl;

or $R^3$, $R^4$ and adjacent nitrogen atoms together form a substituted or unsubstituted 5-12 membered heterocyclyl, wherein, the 5-12 membered heterocyclyl has 1-2 nitrogen atoms, and 0-2 heteroatoms selected from O, S;

the "substituted" means that one or more hydrogen atoms (preferably hydrogen atoms on the nitrogen atom) on the groups are substituted by substituents selected from the group consisting of C1-C4 alkyl, C1-C4 haloalkyl, amine protecting group (preferably tert-butoxycarbonyl), halogen, phenyl;

$R^2$ is selected from the group consisting of H, Cl, Br, C1-C4 alkyl;

the "substituted" means that one or more hydrogen atoms on the groups are substituted by substituents selected from the group consisting of C1-C4 alkyl, C1-C4 haloalkyl, amine protecting group (preferably tert-butoxycarbonyl), halogen;

and when $R^1$ is hydrogen or fluorine, $R^2$ is —$NR^3R^4$, or —(C1-C6 alkyl) —$NR^3R^4$; or when $R^2$ is H, Cl, Br, C1-C4 alkyl, $R^1$ is —(C1-C6 alkyl)-substituted or unsubstituted 5-12 membered heterocyclyl;

and when $R^2$ is H, $R^1$ is other than

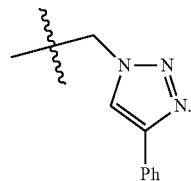 [SMILES: *Cn1cc(-c2ccccc2)nn1]

In another preferred embodiment, at least one of $R^1$ and $R^2$ is

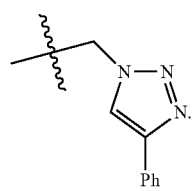 [SMILES: *Cn1cc(-c2ccccc2)nn1]

In another preferred embodiment, the 5-12 membered heterocyclyl is selected from the group consisting of substituted or unsubstituted pyridine, substituted or unsubstituted pyrimidine, substituted or unsubstituted pyridazine, substituted or unsubstituted tetrazine, substituted or unsubstituted pyrrole, substituted or unsubstituted thiophene, substituted or unsubstituted furan, substituted or unsubstituted triazole, substituted or unsubstituted imidazole, substituted or unsubstituted thiazole, substituted or unsubstituted oxazole, substituted or unsubstituted pyrazole, substituted or unsubstituted isothiazole, substituted or unsubstituted isoxazole, substituted or unsubstituted oxadiazole, substituted or unsubstituted thiadiazole, substituted or unsubstituted substituted indole, substituted or unsubstituted indazole, substituted or unsubstituted quinoline, substituted or unsubstituted isoquinoline, substituted or unsubstituted benzofuran, substituted or unsubstituted benzothiophene, substituted or unsubstituted benzimidazole, substituted or unsubstituted benzoxazole, substituted or unsubstituted benzothiazole, substituted or unsubstituted benzoisothiazole, substituted or unsubstituted benzoisoxazole, substituted or unsubstituted benzotriazole, substituted or unsubstituted morpholine, substituted or unsubstituted dihydropiperidine, substituted or unsubstituted thiomorpholine, substituted or unsubstituted piperidine, substituted or unsubstituted piperazine, substituted or unsubstituted tetrahydropyran, substituted or unsubstituted dihydropyran, substituted or unsubstituted pyrroline, substituted or unsubstituted tetrahydrothiophene, substituted or unsubstituted tetrahydrofuran, substituted or unsubstituted oxetane, substituted or unsubstituted thietane, substituted or unsubstituted azetidine.

In another preferred embodiment, the 5-12 membered heterocyclyl is a substituent formed by the ring selected from the group consisting of

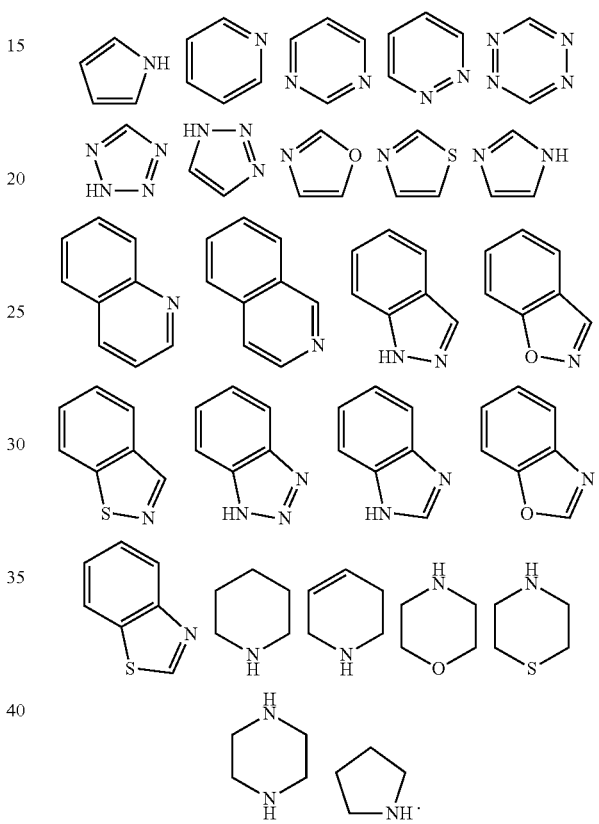

In another preferred embodiment, the compound of formula A1 is selected from the following group:

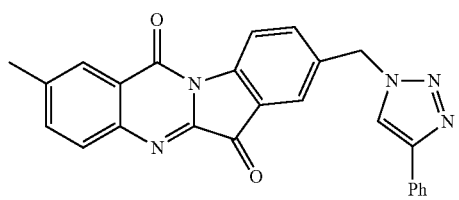

3d

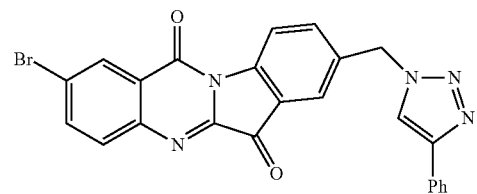

3e

-continued

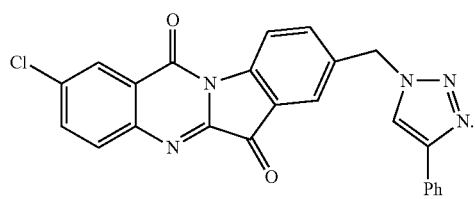
3f

In the fourth aspect of the present invention, a preparation method for compound according to the third aspect of the present invention is provided, which comprises the following steps:

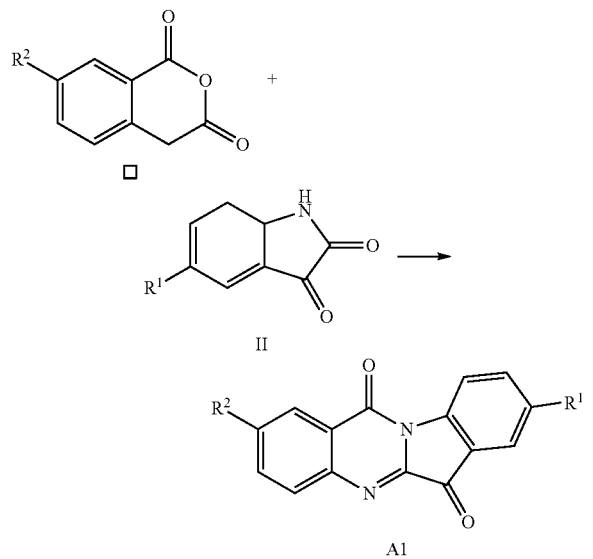

reacting the compound of formula III with the compound of formula II to provide the compound of formula A1;

In each formula, each group is defined as in the third aspect of the present invention.

In the fourth aspect of the present invention, a pharmaceutical composition is provided, comprising (i) the N-benzyl tryptanthrin derivative, or a pharmaceutically acceptable salt thereof according to the third aspect of the invention; and (ii) a pharmaceutically acceptable carrier.

In another preferred embodiment, the pharmaceutical composition is used to treat diseases related to the activity or expression amount of IDO1, IDO2 or TDO.

In another preferred embodiment, the IDO1, IDO2 or TDO is human IDO1, IDO2 or TDO.

In the fifth aspect of the present invention, a use of the compound according to the third aspect of the invention in preparing a pharmaceutical composition or formulation for inhibiting target protein activity is provided, wherein, the target protein is selected from the group consisting of TDO, IDO2, and combinations thereof.

In the sixth aspect of the present invention, a use of tryptanthrin derivative of formula A1, or a pharmaceutically acceptable salt in preparing a pharmaceutical composition or formulation for inhibiting IDO2 activity is provided;

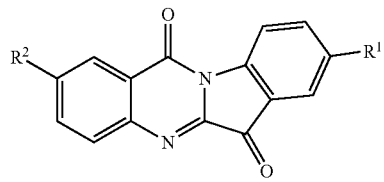
A1 wherein,
$R^1$ is F or

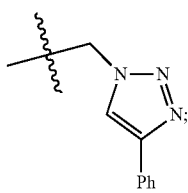 [SMILES: *Cn1cc(-c2ccccc2)nn1]

$R^2$ is selected from the group consisting of H, Cl, Br, C1-C4 alkyl,

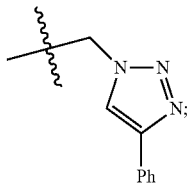 [SMILES: *Cn1cc(-c2ccccc2)nn1]

and one of $R^1$ and $R^2$ is

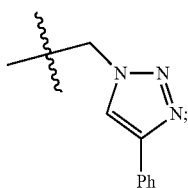 [SMILES: *Cn1cc(-c2ccccc2)nn1]

the "substituted" means that one or more hydrogen atoms on the groups are substituted by group selected from the group consisting of C1-C4 alkyl, C1-C4 haloalkyl, amine protecting group (preferably tert-butoxycarbonyl), halogen;

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Based on a long-term and intensive research, the inventors have unexpectedly found that a class of N-benzyl tryptanthrin derivative of formula 1 has quite excellent TDO inhibitory activity, and thus can be used as a dual IDO/TDO inhibitor, and has a good application prospect. The inventors have completed the present invention on this basis.

Terms

As used herein, unless specifically stated herein, the term "substituted" means that one or more hydrogen atoms on the groups are substituted by group selected from the group consisting of C1-C10 alkyl, C3-C10 cycloalkyl, C1-C10 alkoxy, halogen, hydroxyl, carboxyl (—COOH), C1-C10 aldehyde group, C2-C10 acyl group, C2-C10 ester group, amino group, phenyl; the phenyl contains unsubstituted phenyl or substituted phenyl having 1-3 substituents, the substituent is selected from the group consisting of halogen, C1-C10 alkyl, cyano, OH, nitro, C3-C10 cycloalkyl, C1-C10 alkoxy, and amino.

The term "C1-C6 alkyl" refers to a linear or branched chain alkyl with 1 to 6 carbon atoms, such as methyl, ethyl, propyl, isopropyl, butyl, isobutyl, sec-butyl, tert-butyl, or the like.

The term "5-12 membered heterocyclyl" refers to a saturated or unsaturated (including aromatic) cyclo substitution with one or more heteroatoms selected from O, S, N or P on the 5-12 membered ring, such as pyridyl, thienyl, piperidinyl, or the like, preferably 5-9-membered heterocyclyl.

The term "halogen" refers to F, Cl, Br, and I.

As used herein, the term "contain", "comprise", or "comprising", means that various components can be applied together in a mixture or composition of the present invention. Therefore, the term "mainly composed of" and "consisted of" are included in the term "contain".

As used herein, the term "pharmaceutically acceptable" carrier refers to a substance suitable for human and/or animals without excessive adverse side effects (such as toxicity, irritation and allergy), i.e, with reasonable benefit/risk ratio.

As used herein, the term "effective amount" refers to an amount in which the therapeutic agents can treat, relieve or prevent the targeted disease, or exhibit detectable treatment or prevention effects. The exact effective amount for a subject will depend on the size and health condition of the subject, the nature and extent of the disorder, and the therapeutic agent and/or therapeutic agent combination selected for administration. Therefore, it is useless to specify an accurate effective amount in advance. However, for a given situation, the effective amount may be determined by routine experimentation, which can be determined by clinicians.

As used herein, unless specifically stated herein, the term "substituted" means that one or more hydrogen atoms on the groups are substituted by group selected from the group consisting of halogen, unsubstituted or halo C1-C6 alkyl, unsubstituted or halo C2-C6 acyl, unsubstituted or halo C1-C6 alkyl-hydroxyl.

Unless specifically stated herein, all compounds present in the present invention are intended to include all possible optical isomers, such as monochiral compounds, or mixtures (ie, a racemate) of various chiral compounds. Among all the compounds of the present invention, each chiral carbon atom can optionally be R configuration or S configuration, or a mixture of R and S configurations.

N-benzyl tryptanthrin Derivative

Tryptanthrin is an indoloquinazoline alkaloid, and its chemical name is indole [2,1-b] quinazoline-6, 12-dione. Tryptamine is a yellow acicular crystal, which is mainly found in Isatis indigotica plants such as Strobilanthes cusia (Nees) Kuntze, Polygonum tinctorium Ait, Isatis indigotica Fortune, etc. Tryptanthrin can also be extracted from microbe broths.

The N-benzyl tryptanthrin derivative used in the present invention can be prepared or extracted by methods known in the art.

Terms

As used herein, "compound of the present invention", "tryptanthrin and its derivatives of the present invention", "compound of the formula A1" can be used interchangeably and refer to compound of formula A1, or a racemate, a enantiomer thereof, or a pharmaceutically acceptable salt thereof. It should be understood that the term also includes mixtures of the above components.

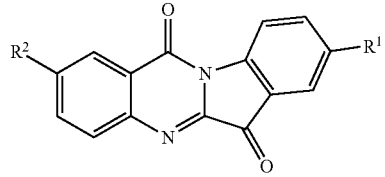

A1

In the formula, each group is defined as above.

The compound of the present invention not only have an inhibiting effect on TDO, but also have a certain inhibiting effect on IDO1. However, it should be noted that not all IDO1 inhibitors would have TDO inhibiting effect. For example, the inhibitor L-1-MT known in the art is a single IDO1 inhibitor.

In the present invention, a pharmaceutically acceptable salt of compound of formula I is also contained. The term "pharmaceutically acceptable salt" refers to a salt suitable for use as a medicament formed by the compound of the present invention with an acid or base. The pharmaceutically acceptable salts include inorganic and organic salts. Preferred salts are salts formed by the compounds of the present invention and acid. Suitable salt-forming acids include, but are not limited to: inorganic acids such as hydrochloric acid, hydrobromic acid, hydrofluoric acid, sulfuric acid, nitric acid, phosphoric acid, etc; organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid , etc; and acidic amino acids such as aspartic acid, glutamic acid.

Composition and Method of Administration

The present invention provides a composition for inhibiting tryptophan dioxygenase. The composition contains, but is not limited to, pharmaceutical composition, food composition, dietary supplement, beverage composition, etc.

In the present invention, the pharmaceutical composition can be directly used for treating diseases, for example, for anti-tumor treatment. When using the pharmaceutically formulation of the present invention, other therapeutic agents, such as anti-tumor drugs, can also be used simultaneously.

The invention also provides a pharmaceutical composition comprising a safe and effective amount of compound of the present invention and a pharmaceutically acceptable carrier or excipient. Such carrier contains, but is not limited to, saline, buffer, glucose, water, glycerol, ethanol, powder, and combinations thereof. The pharmaceutical formulation should match the mode of administration.

Taking the pharmaceutical composition as an example, the composition of the present invention can be prepared in the form of injection, for example, it can be prepared by a conventional method using physiological saline or aqueous solution containing glucose and other adjuvants. Pharmaceutical compositions such as tablet and capsule can be prepared by conventional methods. Pharmaceutical compositions such as injection, solution, tablet and capsule can be prepared under sterile conditions. The pharmaceutical combination of the present invention can also be made into a powder for aerosol inhalation. The active ingredient is administered in a therapeutically effective amount, for example, about 1 µg/kg body weight to about 5 mg/kg body weight per day. In addition, the tryptophan dioxygenase inhibitors of the present invention can also be used with other therapeutic agents.

For the pharmaceutical composition of the present invention, it can be administered to desired subject (such as human and non-human mammals) in a conventional manner. Representative modes of administration contain, but are not limited to, oral, injection, aerosol inhalation, etc.

When the pharmaceutical composition is used, a safe and effective amount of drug is administered to mammals, wherein the safe and effective amount is usually at least about 10 µg/kg body weight, and in most cases no more than about 8 mg/kg body weight, preferably, the dose is about 10 µg/kg body weight to about 1 mg/kg body weight. Of course, the determination of specific dose should also consider factors such as administration route, patient's health status, etc, which are well within the skills of an experienced physician.

Compared with the prior art, the main advantages of the present invention include:

(a) The compound of formula A1 of the present invention has a better inhibiting effect on TDO.

(b) The compound of formula A1 of the present invention can also inhibit IDO1 and therefore can be used as a dual target inhibitor of IDO1/TDO.

(c) The present invention also provides a class of TDO inhibitors with novel structure and a preparation method thereof. The TDO inhibitors have IDO1, IDO2, and TDO inhibiting activities simultaneously, so they can be used to completely block tryptophan metabolism kynurenine pathway.

(d) The present invention provides a new method for treating TDO-related diseases.

(e) The present invention provides a new method for treating tryptophan metabolic disorders mediated by IDO1 and TDO.

(f) The present invention provides a new method for treating tryptophan metabolic disorders mediated by IDO2.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weigh.

Some compounds can be synthesized with reference to existing methods, such as the method described in Chinese Patent no. 201310560572.0.

Synthesis of N-benzyl tryptanthrin Derivative

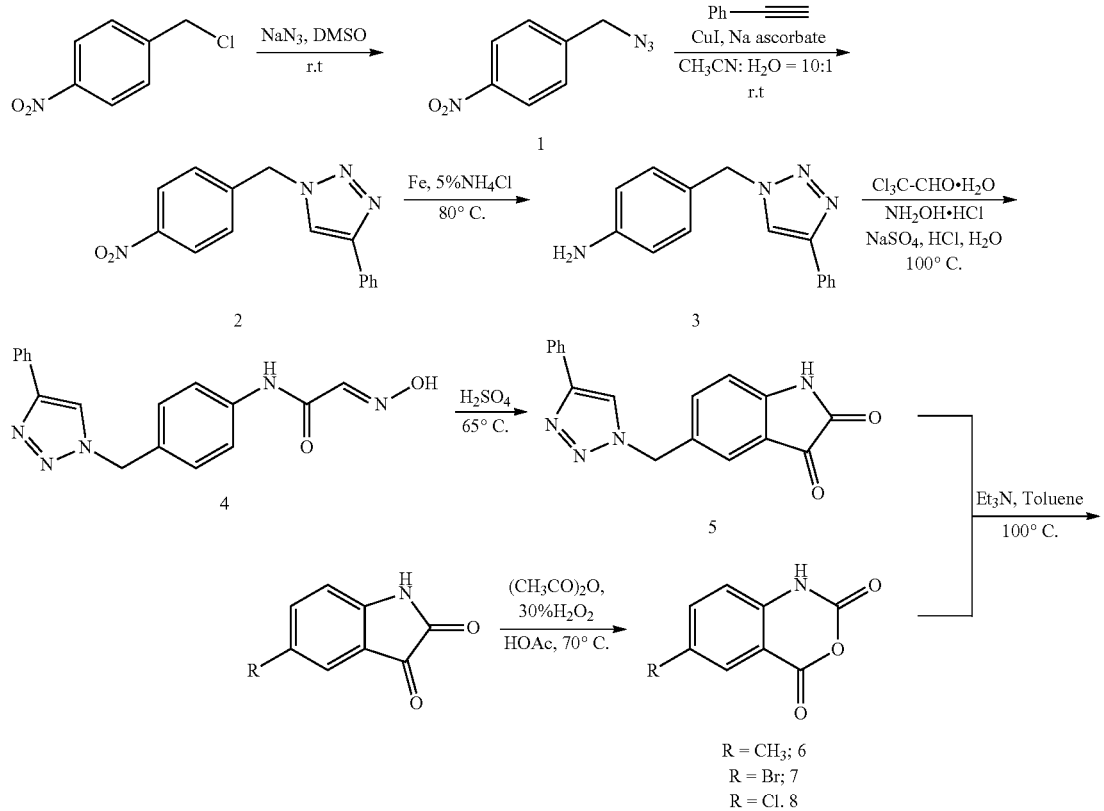

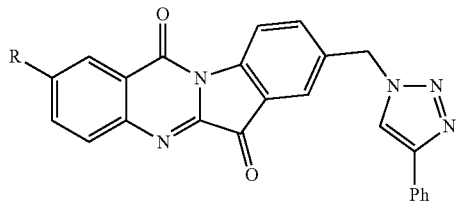

R = CH₃; IV3d
R = Br; V3e
R = Cl. V3f

Reaction Route

In the synthesis route, 4-nitrobenzyl chloride as the starting material was reacted with sodium azide to give 4-nitrobenzyl-azide 1, then triazole 2 was prepared by 1,3-dipolar cycloaddition reaction of 4-nitrobenzyl-azide 1 and phenylacetylene catalyzed under cuprous iodide and sodium ascorbate; after the nitro in triazole 2 was reduced to amino with iron powder, then obtained compound was reacted with trichloroacetaldehyde and hydroxylamine hydrochloride to give oxime 4; oxime 4 is ring-closed under the sulfuric acid to give triazolium-containing indoloquinone 5. Finally, the triazolium-containing indoloquinone 5 is condensed with methyl, bromo, chloro-substituted isatoic anhydride derivatives to give three tryptanthrin derivative (3d, 3e, 3f).

1. Indoloquinone of triazole

Synthetic Route

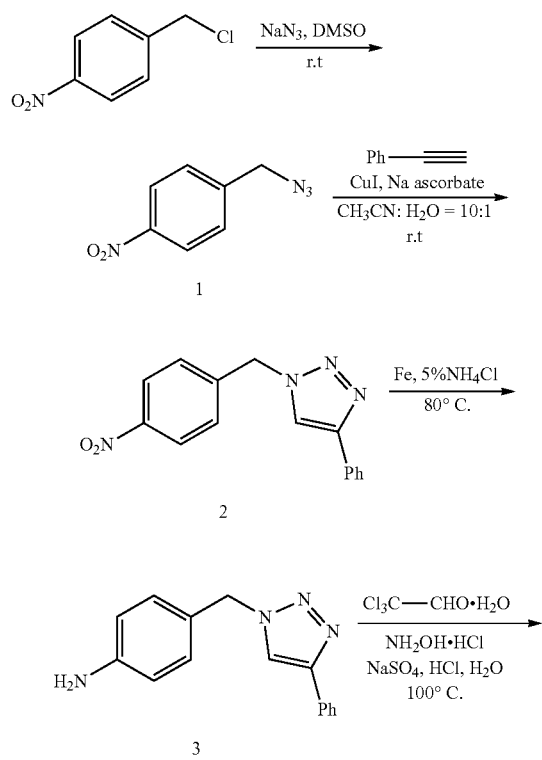

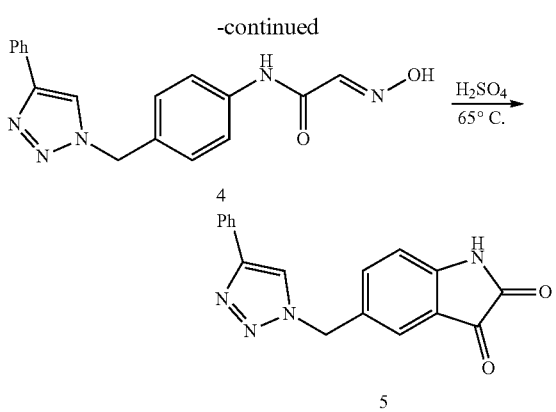

Reaction Steps

1) Preparation of 1-azidomethyl-4-nitrobenzene 1

4-nitrobenzyl chloride (162 mg, 1 mmol), sodium azide (78 mg, 1.2 mmol), and dimethyl sulfoxide (2 mL) were successively added to reaction flask, the reaction mixture was protected from light with aluminum foil and reacted at room temperature for 1 h. After TLC monitored that the reaction was completed, water was added to the reaction system, and ethyl acetate was added for extraction. The organic phase was washed with water, dried over anhydrous $Na_2SO_4$. The ethyl acetate was removed by rotary evaporation under vacuum to give a light yellow-brown liquid 1, which was directly used for the next step.

2) Preparation of 1-(4-nitrophenyl) -4-phenyl-1H-1, 2, 3-triazole (2)

P-nitrobenzyl azide (178 mg, 1 mmol), sodium ascorbate (79 mg, 0.4 mmol), cuprous iodide (38 mg, 0.2 mmol), acetonitrile (3 mL), water (0.3 mL), and phenylacetylene (204 mg, 2 mmol) were successively added to reaction flask, protected by nitrogen, and the reaction mixture was stirred at room temperature overnight. After TLC monitored that the reaction was completed, the reaction solution was poured into water, extracted with ethyl acetate, and washed with saturated brine to neutral. The organic phase was dried over anhydrous sodium sulfate, and the ethyl acetate was removed by rotary evaporation under vacuum, then separated by silica gel column chromatography to give the light yellow crystal 2 224 mg, yield 80%.

The characterization data are as follows:

¹HNMR (400 MHz, CDCl₃): δ=8.24(d, 2H), 7.83(d, 2H), 7.75(s, 1H), 7.44(m, 4H), 7.35(m, 1H), 5.71(s, 2H)

3) Preparation of 4-((4-phenyl-1H-phenyl-1H-1,2,3-triazol-1-yl) methyl) benzenamine 3

Reduced iron powder (448 mg, 8 mmol), ammonium chloride (350 mg, 6.54 mmol) and water (7 mL) were added to reaction flask, the reaction mixture was heated to 100° C. to activate the iron powder for 1 h, then cooled to 80° C. The product (280 mg, 1 mmol) obtained from the previous step was slowly added in batches and reacted for 5 h. After TLC monitored that the reaction was completed, the reaction mixture was cooled to room temperature. Solid sodium carbonate was added to adjust pH =8-9, and 20 ml ethyl acetate was added and stirred for 0.5 h, then filtered through celite. The filtrate was extracted with ethyl acetate, washed with saturated brine to neutral. The organic phase was dried with anhydrous sodium sulfate, and the ethyl acetate was removed by rotary evaporation under vacuum to give the yellow solid 3 228 mg, yield 91%.

The characterization data are as follows:

¹HNMR (400 MHz, CDCl₃): δ=7.79(d, 2H), 7.60(s, 1H), 7.39(t, 2H), 7.30(t, 1H), 7.13(d, 2H), 6.68(d, 2H), 5.44(s, 2H)

4) Preparation of (4-phenyl-1H-1,2,3-triazol-1-methylene) oxime (4)

Trichloroacetaldehyde hydrate (165 mg, 1 mmol), anhydrous sodium sulfate (141 mg, 1 mmol) and water (2.2 mL) was added to reaction flask. The product (250 mg, 1 mmol) obtained from the previous step was added under stirring, and 5% hydrochloric acid (0.7 mL) was added, then hydroxylamine hydrochloride (209 mg, 3 mmol ) and water (0.95 mL) were added, and the reaction mixture was heated to 100° C. After TLC monitored that the reaction was completed, the reaction mixture was cooled to room temperature and suction filtered. The filter cake was successively washed with 10% hydrochloric acid solution and water, and the obtained solid was dried under vacuum to give light yellow solid 4 161 mg, yield 50%.

5) Preparation of (4-phenyl-1H-1,2,3-triazol-1-methylene) indolequinone (5)

Concentrated sulfuric acid (2.5 mL) was added to the reaction flask, the product obtained from the previous step (320 mg, 1 mmol) was added in batches under stirring until completely dissolved. The reaction mixture was heated to 65° C. to react for 5 h. After TLC monitored that the reaction was completed, the reaction solution was poured into water to precipitate a yellow solid and suction filtered, the filter cake was washed with water, then the obtained solid was dried under vacuum to give orange-yellow solid 5 289 mg, yield 95%.

The characterization data are as follows:

¹HNMR (400 MHz, CDCl₃): δ=7.97(s, 1 H), 7.80(d, 3 H), 7.73(s, 1 H), 7.61(s, 1 H), 7.55(d, 1 H), 7.50(d, 2 H), 6.93(d, 1 H), 5.55(s, 2 H)

2. Synthesis of isatoic anhydride

Synthetic Route

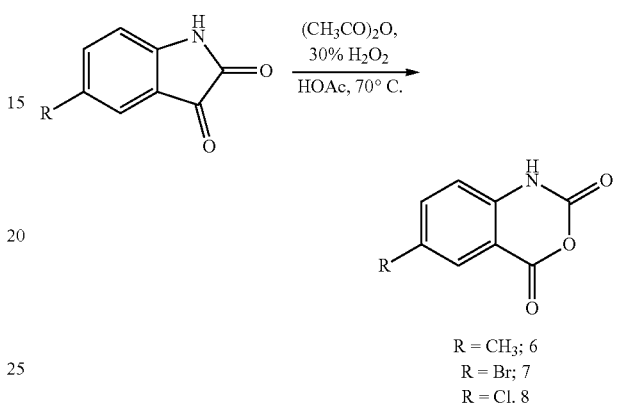

R = CH₃; 6
R = Br; 7
R = Cl. 8

Reaction Steps

1) Synthesis of 5-methylisatoic anhydride 6

Acetic acid (1 mL) and concentrated sulfuric acid (0.05 mL) were added to reaction flask, 5-methylindolequinone (161 mg, 1 mmol) was added in batches under stirring, then the mixture of acetic anhydride (0.2 ml ) and 30% hydrogen peroxide (0.23 ml ) was started to add, the reaction solution was heated to 70° C. for 4 h. After TLC monitored that the reaction was completed, the reaction mixture was cooled and suction filtered, the filter cake was successively washed with water, 5% sodium bicarbonate solution and water, the obtained solid was dried under vacuum to give orange-yellow solid 6 135 mg, yield 76.3%.

2) Synthesis of 5-bromo isatoic anhydride 7

Acetic acid (1 mL) and concentrated sulfuric acid (0.05 mL) were added to reaction flask, 5-bromoindoloquinone (226 mg, 1 mmol) was added in batches under stirring, then started to add the mixture of acetic anhydride (0.2 ml) and 30% hydrogen peroxide (0.23 ml ), the reaction solution was heated to 70° C. for 4 h. After TLC monitored that the reaction was completed, the reaction mixture was cooled and suction filtered, the filter cake was successively washed with water, 5% sodium bicarbonate solution and water, the obtained solid was dried under vacuum to give light yellow solid 7 194 mg, yield 80.1%.

3) Synthesis of 5-chloro isatoic anhydride (8)

Acetic acid (1 mL) and concentrated sulfuric acid (0.05 mL) were added to reaction flask, 5-chloroindoloquinone (181 mg, 1 mmol) was added in batches under stirring, then started to add the mixture of acetic anhydride (0.2 ml ) and 30% hydrogen peroxide (0.23 ml ), the reaction solution was heated to 70° C. for 4 h. After TLC monitored that the reaction was completed, the reaction mixture was cooled and suction filtered, the filter cake was successively washed with water, 5% sodium bicarbonate solution and water, the obtained solid was dried under vacuum to give light yellow solid 8 135 mg, yield 68.2%.

3. Synthesis of N-benzyl tryptanthrin derivative 3d-3f

Synthetic Route

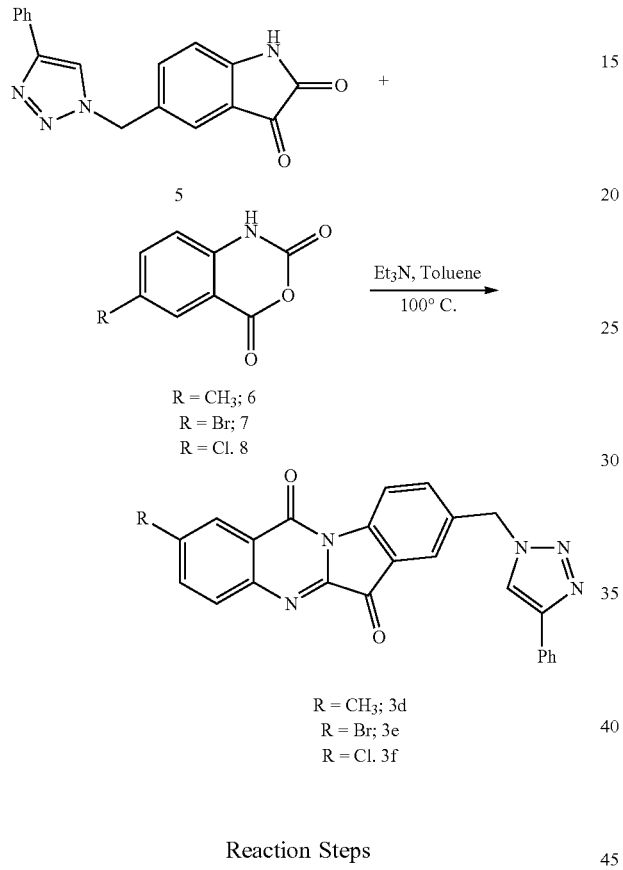

R = CH₃; 6
R = Br; 7
R = Cl. 8

R = CH₃; 3d
R = Br; 3e
R = Cl. 3f

Reaction Steps

1) Synthesis of 8-(4-phenyl-1H-1,2,3-triazol-1-methylene) -2-methyltryptanthrin (3d)

Triazolium-containing indoloquinone 5 (304 mg, 1 mmol), 5-methylisatoic anhydride (177 mg, 1 mmol), triethylamine (505 mg, 5 mmol) and toluene (2.5 mL) were successively added to reaction flask, the reaction mixture was heated to 110° C. and stirred at reflux for 4 h. After TLC monitored that the reaction was completed, the triethylamine and toluene were removed by rotary evaporation under vacuum, and recrystallized with anhydrous ethanol to give yellow-green solid 3d 315 mg, yield 75.1%.

The characterization data are as follows:
$^1$HNMR (400 MHz, CDCl$_3$): δ=8.66(d, 1 H), 8.23(s, 1 H), 7.91(d, 1 H), 7.84(t, 3 H) 7.76(t, 2 H), 7.67(d, 1 H), 7.42(t, 2 H), 7.34(t, 1 H), 5.68(s, 2 H), 2.56(s, 3 H).

2) Synthesis of 8-(4-phenyl-1H-1,2,3-triazol-1-methylene) -2-bromotryptanthrin 3e Triazolium-containing indoloquinone 5 (304 mg, 1 mmol), 5-bromoisatoic anhydride (197 mg, 1 mmol), triethylamine (505 mg, 5 mmol) and toluene (2.5 mL) were successively added to reaction flask, the reaction mixture was heated to 110° C. and stirred at reflux for 4 h. After TLC monitored that the reaction was completed, the triethylamine and toluene were removed by rotary evaporation under vacuum, and recrystallized with anhydrous ethanol to give yellow-green solid 3e 343 mg, yield 70.8%.

The characterization data are as follows:
$^1$HNMR (400 MHz, CDCl$_3$): δ=8.61(d, 1 H), 8.27(s, 1 H), 8.01(d, 1 H), 7.81(t, 3 H) 7.78(t, 2 H), 7.54(d, 1 H), 7.47(t, 2 H), 7.31(t, 1 H), 5.69(s, 2 H).

3) Synthesis of 8-(4-phenyl-1H-1,2,3-triazol-1-methylene) -2-chlorotryptanthrin (3f)

Triazolium-containing indoloquinone 5 (304 mg, 1 mmol), 5-chloroisatoic anhydride (242 mg, 1 mmol), triethylamine (505 mg, 5 mmol) and toluene (2.5 mL) were successively added to 25 ml reaction flask, the reaction mixture was heated to 110° C. and was stirred at reflux for 4 h. After TLC monitored that the reaction was completed, the triethylamine and toluene were removed by rotary evaporation under vacuum, and recrystallized with anhydrous ethanol to give yellow-green solid 3f 340 mg, yield 77.3%.

The characterization data are as follows:
$^1$HNMR (400 MHz, CDCl$_3$): δ=8.61(d, 1 H), 8.25(s, 1 H), 7.92(d, 1 H), 7.83(t, 3 H) 7.76(t, 2 H), 7.63(d, 1 H), 7.45(t, 2 H), 7.33(t, 1 H), 5.65(s, 2 H).

ACTIVITY EXAMPLES

General Materials

The nucleotide sequences of IDO1, IDO2, and TDO have been disclosed. The active IDO1, IDO2, and TDO in the Examples are human IDO1, IDO2, and TDO, and can be prepared by conventional molecular cloning methods.

The IC$_{50}$ test of IDO1 can be performed with reference to existing methods in the art, such as the method described in Chinese Patent NO. 201310560572.0.

Example 1

Determination of Half Effective Inhibitory Concentration IC$_{50}$ (Enzyme Level) of IDO2

In a 500 μL standard detection system, 50 mmol/L potassium phosphate buffer (pH 7.5), 200 μg/mL catalase, 40 mmol/L ascorbic acid, 20 μmol/L methylene blue, substrate L-tryptophan with suitable concentration and IDO2 inhibitors to be tested (including the compound of the present invention, L-1-MT and D-1-MT) with a final concentration of 10 μM were mixed. After the mixed solution was in water bath at 37° C. for 5 min, IDO2 was added to mixed solution and reacted at 37° C. for 30 min. After the enzymatic reaction was completed, 200 μL of 30% (w/v) trichloroacetic acid was added to terminate the reaction. Then the reaction mixture was heated in a 65° C. water bath for 15 min to make the reaction product transform from N-formyl-kynurenine to kynurenine, and centrifuged at 138000×g for 10 min. 100 μL of supernatant was draw and mixed with equal volume of 2‰ (w/v) p-dimethylaminobenzaldehyde in acetic acid completely. The kynurenine can react with the solution and turn the mixed solution to yellow, and the absorbance was measured at 492 nm by microplate reader.

Under pH 7.5, the inhibiting rate of the compounds of the present invention on IDO2 were significantly higher than those of L-1-MT and D-1-MT. The preliminary screening results of the compound of this embodiment provided a basis for data verification for subsequent determination of IC50 value, Ki value, and determination of inhibition type.

Example 2

Determination of IDO2 Inhibitor Type and Ki Value

In the 500 μL detection system of Example 1, the substrate L-tryptophan at different concentrations (20, 30, 40 mM or 20, 25, 35 mM) was added respectively, test inhibitors (including the compounds of the present invention, L-1-MT and D-1-MT) at different concentrations were added to each substrate concentration, while the control group without inhibitors. After the mixed solution was in water bath at 37° C. for 5 min, 10 μL of IDO2 (about 1 μM) was added to mixed solution and reacted at 37° C. for 30 min. After the enzymatic reaction was completed, 200 μL of 30% (w/v) trichloroacetic acid was added to terminate the reaction. Then the reaction mixture was heated in 65° C. water bath for 15 min to make the reaction product transform from N-formyl-kynurenine to kynurenine, and centrifuged at 138000×g for 10 min. 100 μL of supernatant was draw and mixed with equal volume of 2‰ (w/v) p-dimethylamino-benzaldehyde in acetic acid completely. The kynurenine can react with the solution and turn the mixed solution to yellow, and the absorbance was measured at 492 nm by microplate reader. The inhibitor type was determined by Dixon mapping method (1/v~[i]); the Ki value of inhibitor was obtained by [S]/V~[i] map.

Example 3

Determination of Half Effective Inhibitory Concentration IC50 (Cell) of IDO2

U87 MG cell line (ATCC No.: HTB-14) was cultured in DMEM high-sugar medium containing 10% fetal bovine serum in a 37° C., 5% $CO_2$ incubator. The cells were blown evenly into 6-well plate, and transfected when the cells grew to 80%-90% fusion. The operation was carried out according to the instructions of Lipofectamine 2000 while slightly improved: the serum-containing medium was draw out and the cells were washed twice with PBS, and 1500 μL of serum-free medium was added to each well. Plasmid and liposome were added to EP tube pre-loaded with 125 μL of Opti-MEM medium at a ratio of 1:2 (2.5 ng plasmid and 5 μL liposome per well) respectively, and mixed gently. After 5 min, the plasmid and liposome were mixed, and added to the culture medium with cells to be transfected dropwise after incubated at room temperature for 20 minutes. The cells were cultured in 37° C., 5% $CO_2$ incubator for 6 h, and the medium was changed into DMEM medium containing 10% serum after adherence. After incubated for 18 h, cells were seeded in 96-well plate at a density of 2.5 ×$10^4$ cells/well, and cultured in incubator at 37° C., 95% humidity, and 5% $CO_2$ for 6 h. Test compounds (including compounds of the present invention, L-1-MT and D-1-MT) at different concentration gradients were added and the total volume of each well was supplemented to 200 μl with cell culture medium containing L-tryptophan (200 μM of final concentration, sterilized by filtration). After incubated for 24 h, 140 μL of supernatant was taken into another 96-well plate, 10 μL of 30% (w/v) trichloroacetic acid was added, heated at 65° C. for 15 min, and centrifuged at 13800×g for 5 minutes. 100 μL of supernatant was mixed with equal volume of 2‰ (w/v) p-diaminobenzaldehyde in acetic acid, the absorbance was measured at 492 nm by microplate reader after fully mixed. The experimental grouping was pcDNA3.1 (+)–IDO2 transfected group (experimental group), pcDNA3.1 (+) transfected group (empty plasmid control group), and non-transfected group (blank control group). Each group had three repeated well. The inhibitory rate was plotted against the inhibitor concentration, and the $IC_{50}$ value was calculated by modified Karber method.

Example 4

Determination of Half Effective Inhibitory Concentration $IC_{50}$ (Enzyme Level) of TDO In a 500 μL of standard detection system, 50 mmol/L potassium phosphate buffer (pH 7.0), 200 μg/mL catalase, 40 mmol/L ascorbic acid, 20 μmol/L methylene blue, substrate L-tryptophan with suitable concentration and hTDO inhibitors to be tested were mixed. After the mixed solution was warmed in water bath at 37° C. for 5 min, hTDO was added to react at 37° C. for 30 min. After the enzymatic reaction was completed, 100 μ30% (w/v) trichloroacetic acid was added to terminate the reaction. Then the reaction mixture was heated in a 65° C. water bath for 15 min to make the reaction product transform from N-formyl-kynurenine to kynurenine, and centrifuged at 138000×g for 10 min. 100 μL of supernatant was draw and mixed with equal volume of 2‰ (w/v) p-dimethylaminobenzaldehyde in acetic acid completely. The kynurenine can reacted with the solution and turned the mixed solution to yellow, and the absorbance was measured at 492 nm by microplate reader. The inhibitory rate was plotted against the inhibitor concentration, and the $IC_{50}$ value was calculated by modified Karber method, the experimental results were shown in Table 1.

Example 5

Determination of Half Effective Inhibitory Concentration $IC_{50}$ (Cell) of TDO HEK293 cell line was cultured in DMEM high-sugar medium containing 10% fetal bovine serum in a 37° C., 5% $CO_2$ incubator. The cells were blown evenly into 6-well plates, and transfected when the cells grew to 80%-90% fusion. The operation was carried out according to the instructions of Lipofectamine 2000 while improved slightly: the serum-containing medium was draw out and the cells were washed twice with PBS, and 1500 μL of serum-free medium was added to each well. Plasmid and liposome were added to EP tube pre-loaded with 125 μL of Opti-MEM medium at a ratio of 1:2 (2.5 ng plasmid and 5 μL liposome per well) respectively, and mixed gently. After 5 min, the plasmid and liposome were mixed, and added to the culture medium with cells to be transfected dropwise after incubated at room temperature for 20 minutes. The cells were cultured in 37° C., 5% $CO_2$ incubator for 4-6 h, and then the medium was changed into DMEM medium containing 10% serum. After incubated for 12 h, cells were seeded in 96-well plate at a density of 2.5×$10^4$ cells/well, and cultured in incubator at 37° C., 95% humidity, and 5% $CO_2$ for 12 h. Test compounds (including compounds of the present invention, L-1-MT and INCB023460) at different concentration gradients were added and the total volume of each well was supplemented to 200 μl with cell culture medium. After incubated for 5 h, 140 μL of supernatant was taken into another 96-well plate, 10 μL of 30% (w/v) trichloroacetic acid was added, heated at 65° C. for 15 min, and centrifuged at 13800×g for 5 minutes. 100 μL of supernatant was mixed with equal volume of 2‰ (w/v) p-diaminobenzaldehyde acetic acid solution, the absorbance was measured at 492 nm by microplate reader after fully mixing. The experimental grouping was pcDNA3.1 (+)–hTDO transfected group (experimental group), pcDNA3.1 (+) transfected group (plasmid-empty control group), and non-transfected group (blank control group). Each group had three repeated well. The inhibitory rate was plotted against the inhibitor concentration, and the $IC_{50}$ value was calculated by modified Karber method, the experimental results were shown in Table 1.

According to the method of Example 1-5 described above, the IDO1, IDO2, and TDO inhibitory activity of the compounds prepared in Example 1-5 were determined, and the IDO inhibitor 1-methyltryptophan (1-MT, commercially available), which is commonly used in in vivo and in vitro experiments, was used as control. The determination results were shown in Table 1.

TABLE 1

IDO1, IDO2, and TDO inhibitory activities of the N-benzyl tryptanthrin derivative (A1) synthesized in the above examples

| | $IC_{50}$ (uM) | | | | | | Ki (uM) | |
|---|---|---|---|---|---|---|---|---|
| | enzymatic | | | Cellular | | | | |
| compound | IDO1 | IDO2 | TDO | IDO1 | IDO2 | TDO | IDO1 | IDO2 |
| 3a | 45.23 | 98.01 | 46.63 | 0.278 | 48.09 | 0.688 | 103.21 | ND |
| 3b | 50.03 | 99.57 | 81.79 | 0.335 | 50.12 | 1.368 | 96.25 | ND |
| 3c | 39.06 | 83.05 | 39.97 | 0.185 | 41.73 | 0.197 | 63.34 | ND |
| 3d | 82.63 | 134.07 | 88.74 | 0.547 | 68.35 | 1.437 | 98.12 | |
| 3e | 41.07 | 101.54 | 44.56 | 0.201 | 51.16 | 0.715 | ND | ND |
| 3f | 42.23 | 124.53 | 50.15 | 0.245 | 65.12 | 0.713 | ND | ND |
| 1a | 0.50 | 18.44 | 0.76 | 0.022 | 18.66 | 0.093 | 2.64 | 6.32 |
| 1b | 0.68 | 31.45 | 0.87 | 0.074 | 3.58 | 0.092 | 4.12 | 1.96 |
| 1c | 1.88 | 62.61 | 0.45 | 0.133 | 8.05 | 0.067 | 7.21 | 6.11 |
| 1d | 2.52 | 46.86 | 2.41 | 0.177 | 23.29 | 0.184 | 5.97 | 8.85 |
| 1e | 0.11 | 14.03 | 0.41 | $1.01 * 10^{-3}$ | 3.81 | 0.063 | 0.31 | 4.32 |
| 1f | 0.40 | 39.55 | 0.87 | $1.21 * 10^{-3}$ | 16.54 | 0.071 | 0.47 | 17.54 |
| L-1-MT | 380 | 82.53 | NI | 18.4 | 56.96 | NI | 34 | 425 |
| INCB023460 | 0.072 | 10.34 | 59.2 | 0.031 | ND | ND | ND | ND |

Note:
NI means of no inhibitory activity,
ND means undetected.

It could be seen from the above results that the IDO1 inhibitor INCB023460 in clinical trials was of poor inhibitory activity to IDO2 and TDO, especially TDO inhibitory activity, thus being single IDO1 inhibitor. The compound of the present application had good IDO1 inhibitory activity and TDO inhibitory activity, which could be used as a dual IDO1/TDO inhibitor. As learn from the $IC_{50}$ value, the IDO1 inhibitory activity of this type of parent nuclear compounds were basically better than TDO inhibitory activity, such as 1e and 1f, but the TDO inhibitory activity of 1c is even better than IDO1 inhibitory activity.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A method for inhibiting tryptophan dioxygenase activity and indoleamine 2,3-dioxygenase 1 activity in a subject, wherein the method comprises administering to a subject in need thereof a therapeutically effective amount of a compound of formula A1:

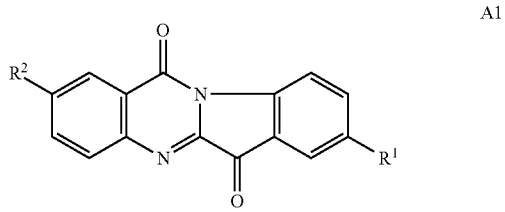

A1 or a pharmaceutically acceptable salt thereof,
wherein:
$R^1$ is H, F, or $C_1$-$C_6$ alkylene-(5- to 12-membered heterocyclyl); wherein the 5- to 12-membered heterocyclyl is selected from the group consisting of pyrrolyl, imidazolyl, oxazolyl, thiazolyl, 1,2,3-triazolyl, tetrazolyl, pyridinyl, pyridazinyl, pyrimidinyl, and 1,2,4,5-tetrazinyl;
wherein the $C_1$-$C_6$ alkylene is optionally substituted with one or more substituents independently selected from the group consisting of halogen, $C_1$-$C_4$ alkyl, $C_1$-$C_4$ haloalkyl, $C(O)OC(CH_3)_3$, and phenyl; and
wherein the pyrrolyl, imidazolyl, oxazolyl, thiazolyl, 1,2,3-triazolyl, tetrazolyl, pyridinyl, pyridazinyl, pyrimidinyl, or 1,2,4,5-tetrazinyl is optionally substituted with one or more substituents independently selected from the group consisting of halogen, $C_1$-$C_4$ alkyl, $C_1$-$C_4$ haloalkyl, $C(O)OC(CH_3)_3$, and phenyl;
$R^2$ is F, Cl, Br, $C_1$-$C_4$ alkyl, $C_1$-$C_6$ alkylene-$NR^3R^4$, or $NR^3R^4$;
wherein the $C_1$-$C_4$ alkyl is optionally substituted with one or more substituents independently selected from the group consisting of halogen, $C_1$-$C_4$ alkyl, $C_1$-$C_4$ haloalkyl, $C(O)OC(CH_3)_3$, and phenyl; and wherein the $C_1$-$C_6$ alkylene is optionally substituted with one or more substituents independently selected from the group consisting of halogen, $C_1$-$C_4$ alkyl, $C_1$-$C_4$ haloalkyl, $C(O)OC(CH_3)_3$, and phenyl;

$R^3$ is H or $C_1$-$C_4$ alkyl;

wherein the $C_1$-$C_4$ alkyl is optionally substituted with one or more substituents independently selected from the group consisting of halogen, $C_1$-$C_4$ alkyl, $C_1$-$C_4$ haloalkyl, $C(O)OC(CH_3)_3$, and phenyl; and $R^4$ is H or $C_1$-$C_4$ alkyl;

wherein the $C_1$-$C_4$ alkyl is optionally substituted with one or more substituents independently selected from the group consisting of halogen, $C_1$-$C_4$ alkyl, $C_1$-$C_4$ haloalkyl, $C(O)OC(CH_3)_3$, and phenyl; or $R^3$ and $R^4$, taken together with the nitrogen atom to which they are attached, form a 5- to 12-membered heterocyclyl;

wherein the 5- to 12-membered heterocyclyl is selected from the group consisting of pyrrolidin-1-yl, piperidin-1-yl, 1,2,3,6-tetrahydropyridin-1-yl, piperazin-1-yl, morpholin-4-yl, thiomorpholin-4-yl, 1,2,3-triazol-1-yl, and 1,2,3-triazol-2-yl; and wherein the pyrrolidin-1-yl, piperidin-1-yl, 1,2,3,6-tetrahydropyridin-1-yl, piperazin-1-yl, morpholin-4-yl, thiomorpholin-4-yl, 1,2,3-triazol-1-yl, or 1,2,3-triazol-2-yl is optionally substituted with one or more substituents independently selected from the group consisting of halogen, $C_1$-$C_4$ alkyl, $C_1$-$C_4$ haloalkyl, $C(O)OC(CH_3)_3$, and phenyl.

2. The method of claim 1, wherein the subject has a disease mediated by:
(1) tryptophan dioxygenase; or
(2) tryptophan dioxygenase and indoleamine 2,3-dioxygenase 1.

3. The method of claim 1, wherein the subject has a disease selected from the group consisting of Alzheimer's disease, glioma, liver cancer, and a mental disorder.

4. The method of claim 1, wherein the subject has a disease selected from the group consisting of bladder cancer, colon cancer, leukemia, liver cancer, lung cancer, melanoma, myeloma, and pancreatic cancer.

5. The method of claim 1, wherein the subject has a tumor with no expression of indoleamine 2,3-dioxygenase 1.

6. The method of claim 1, wherein:
$R^1$ is $C_1$-$C_6$ alkylene-(1,2,3-triazolyl);
wherein the 1,2,3-triazolyl is optionally substituted with one or more substituents independently selected from the group consisting of $C_1$-$C_4$ alkyl and phenyl.

7. The method of claim 1, wherein:
$R^2$ is F, Cl, Br, $C_1$-$C_4$ alkyl, or $CH_2$—$NR^3R^4$;
$R^3$ is $C_1$-$C_4$ alkyl; and
$R^4$ is $C_1$-$C_4$ alkyl; or
$R^3$ and $R^4$, taken together with the nitrogen atom to which they are attached, form a piperazin-1-yl, morpholin-4-yl, or 1,2,3-triazol-1-yl;
wherein the piperazin-1-yl is optionally substituted with one or more substituents independently selected from the group consisting of $C_1$-$C_4$ alkyl and $C(O)OC(CH_3)_3$; and
wherein the 1,2,3-triazol-1-yl is optionally substituted with one or more substituents independently selected from the group consisting of $C_1$-$C_4$ alkyl and phenyl.

8. The method of claim 1, wherein the compound is selected from the group consisting of:

1a
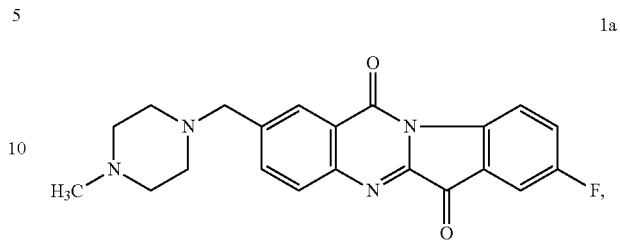

1b
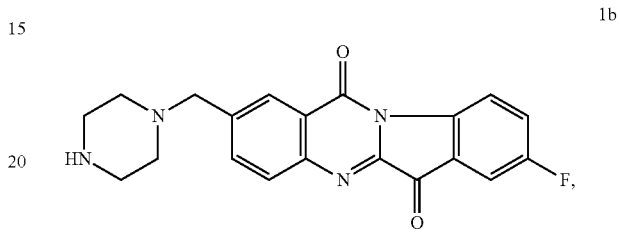

1c
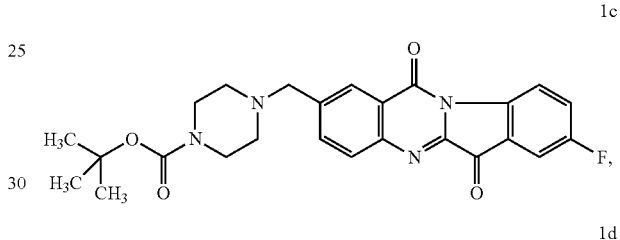

1d
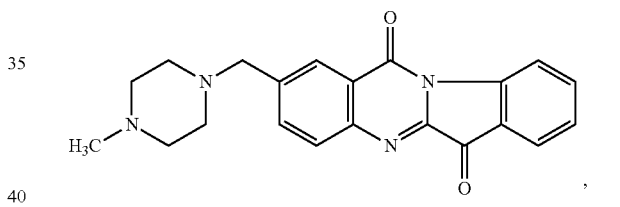

1e
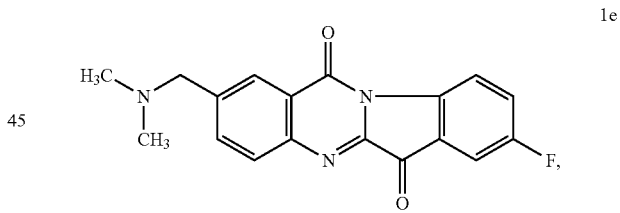

1f

3b
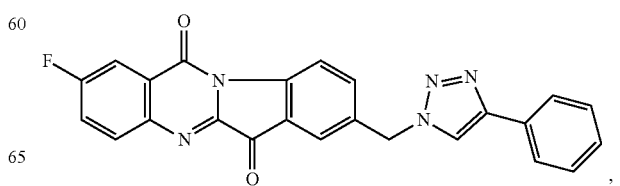

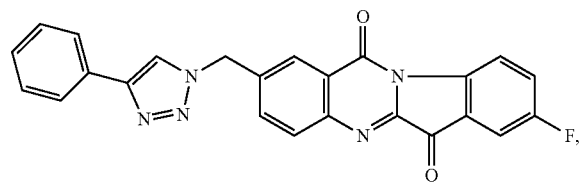
3c
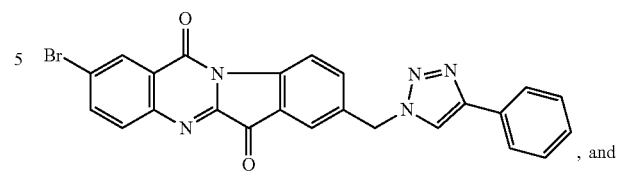
3e
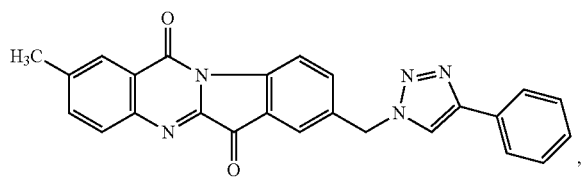
3d
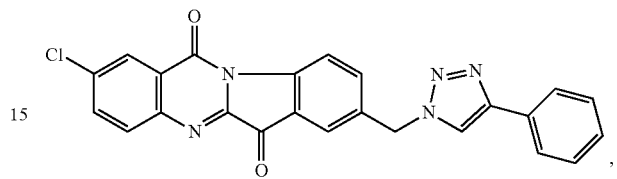
3f
or a pharmaceutically acceptable salt thereof.
* * * * *